United States Patent [19]

Kado et al.

[11] Patent Number: 6,051,212
[45] Date of Patent: Apr. 18, 2000

[54] PROCESS FOR PRODUCING YEAST EXTRACT

[75] Inventors: Hisao Kado; Takumi Shibata; Fujio Kobayashi, all of Yaizu; Masaki Kubota, Nitta-machi, all of Japan

[73] Assignee: Sapporo Breweries Limited, Tokyo, Japan

[21] Appl. No.: 09/147,393

[22] PCT Filed: Apr. 16, 1998

[86] PCT No.: PCT/JP98/01741

§ 371 Date: Dec. 16, 1998

§ 102(e) Date: Dec. 16, 1998

[87] PCT Pub. No.: WO98/46089

PCT Pub. Date: Oct. 22, 1998

[30] Foreign Application Priority Data

Apr. 16, 1997 [JP] Japan ..................................... 9-113648

[51] Int. Cl.[7] .................................. A61K 7/00; A23F 1/00
[52] U.S. Cl. ...................... 424/70.14; 424/401; 426/656; 514/844; 514/846
[58] Field of Search ...................... 426/60, 656; 424/401, 424/70.14; 514/844, 846

[56] References Cited

U.S. PATENT DOCUMENTS

| | | | |
|---|---|---|---|
| 3,962,466 | 6/1976 | Nakabayashi | 426/60 |
| 5,087,449 | 2/1992 | Masai et al. | 424/195.1 |
| 5,258,183 | 11/1993 | Grimberg | 424/401 |
| 5,571,503 | 11/1996 | Mausner | 424/59 |
| 5,650,149 | 7/1997 | Okabe | 424/93.51 |
| 5,667,791 | 9/1997 | Hersh et al. | 424/401 |

FOREIGN PATENT DOCUMENTS

| | | |
|---|---|---|
| 0 688 562 | 12/1995 | European Pat. Off. . |
| 15 17 123 | 9/1969 | Germany . |
| 62-40261 | 2/1987 | Japan . |
| 2-219560 | 9/1990 | Japan . |
| 4-248968 | 9/1992 | Japan . |
| 6-219936 | 8/1994 | Japan . |
| WO 96/38057 | 12/1996 | WIPO . |

OTHER PUBLICATIONS

Derwent Abstracts, AN 76–27115X, JP 51 022834, Feb. 23, 1976.
Derwent Abstracts, AN 93–285366, JP 05 201872, Aug. 10, 1993.
Derwent Abstracts, AN 84–026607, JP 58 216669, Dec. 16, 1983.
Belikov et al. Khim. –Farm. Zh. 1978, vol. 12, No. 6, pp. 126–130.
Drublyanete et al. Sb. Tr., Nauchno–Issled. Inst. Gidroliza Rastit. Mater, 1965, vol. 13, pp. 106–111.

*Primary Examiner*—Sandra E. Saucier
*Assistant Examiner*—Vera Afremova
*Attorney, Agent, or Firm*—Olbon, Spivak, McClelland, Maier & Neustadt, P.C.

[57] ABSTRACT

In accordance with the present invention, it is provided a method for producing a yeast extract with the improvement in the color and odor characteristic to yeast extract and with no modification of the useful substances such as amino acid, etc. compared with conventional yeast extract.

By a simple method in accordance with the present invention, color and characteristic odor can be removed, with almost no loss of the contents of useful substances such as amino acid, etc. from the yeast extract solution produced in a conventional manner. Because the resulting yeast extract can be mixed with other materials for use, the yeast extract is applicable to various fields, for example for cosmetic products and healthy foods other than seasonings, which expectantly enlarges the applicable range of the yeast extract.

20 Claims, 4 Drawing Sheets

PROCESS FOR PRODUCING YEAST EXTRACT

TECHNICAL FIELD

The present invention relates to a method for producing a yeast extract; and more specifically, the present invention relates to a method for producing a yeast extract, comprising integrated processes to actively remove yellow or brown color specific to yeast extract and further optionally remove a characteristic odor of yeast extract, and the present invention additionally relates to a cosmetic product with the yeast extract blended therein.

TECHNICAL BACKGROUND

Yeast extract has been used widely as a seasoning comprising natural materials, and yeast extract has characteristics such that it highly safe and has complex taste such as unique flavor and body which artificial seasonings is absent. In recent years, furthermore, yeast extract has been drawing attention as materials for cosmetics and healthy food, wherein useful amino acids and nucleic acids contained in yeast extract are effectively utilized.

However, yeast extract has unique yellow or brown color and characteristic odor, and these work as factors severely limiting the applicable range of yeast extract or the amount thereof to be used.

For the purpose of removing such color or odor, therefore, various proposals have been made conventionally. For example, the proposals are made about deodorizing by means of hydrophobic resins (Japanese Patent Application No. 131064/1992 etc.), deodorizing by means of enzyme treatment, chemical treatment methods by acids or alkalis (Japanese Patent Laid-open No. 11188/1976 etc.), or yeast selection for producing yeast extract (Japanese Patent Laid-open No. 66861/1974). Although the processes of these methods are very laborious, however, the resulting advantages are poor disadvantageously, so the methods are not so frequently carried out currently.

The reason of the coloring of yeast extract lies in that at the process of producing yeast extract, saccharides (carbohydrates) and amino acids cause aminocarbonyl reaction through the heating process, with the resultant production of a substance colored dark brown. Heating treatment is carried out in the course of producing seasonings and cosmetics from a raw material yeast extract, so those nearly colorless at the stage of raw materials might potentially be colored at the intermediate stage of the production methods.

DISCLOSURE OF THE INVENTION

In accordance with the present invention, therefore, it has been found that the color specific to yeast extract can prominently be reduced by subjecting a yeast extract solution obtained in a conventional manner, to heating treatment to preliminarily generate colored substances in the yeast extract and thereafter separating and removing the colored substances, and thus, the present invention has been achieved.

It is an object of the present invention to provide a method for producing a yeast extract with the improvement in color and odor which are specific to the yeast extract but with useful substances such as amino acid retained therein, and to further actively apply the yeast extract to fields where yeast extract has conventionally been applied with much difficulty.

In a first aspect of the present invention, it is provided a method for producing a yeast extract, comprising a heating process of a yeast extract solution obtained in a conventional manner and an adsorption process of putting the resulting extracts solution colored at said heating process in contact to an ion exchange resin so as to remove the colored substances in the yeast extract solution.

In a second aspect of the present invention, it is provided a method for producing a yeast extract, comprising a heating process of a yeast extract solution obtained in a conventional manner, a filtration process of removing the solids as produced at the heating process and polymeric components in the extract solution and an adsorption process of putting the yeast extract solution in contact to an ion exchange resin so as to remove the colored substances in the extract solution after the filtration process.

In a third aspect of the present invention, it is provided a method for producing a yeast extract, comprising a heating process of a yeast extract solution in water or in hot water, a contact process of putting the colored yeast extract solution in contact to an organic solvent miscible with water to precipitate and remove the high molecular substances and solids in the extract solution, and an adsorption process of putting the extract solution after the contact process in contact to an ion exchange resin to remove the colored substances in the extract solution.

In a fourth aspect of the present invention, additionally, it is provided a cosmetic product characterized by being blended with the yeast extract produced by the inventive method.

BEST MODE FOR CARRYING OUT THE INVENTION

Figure 1:
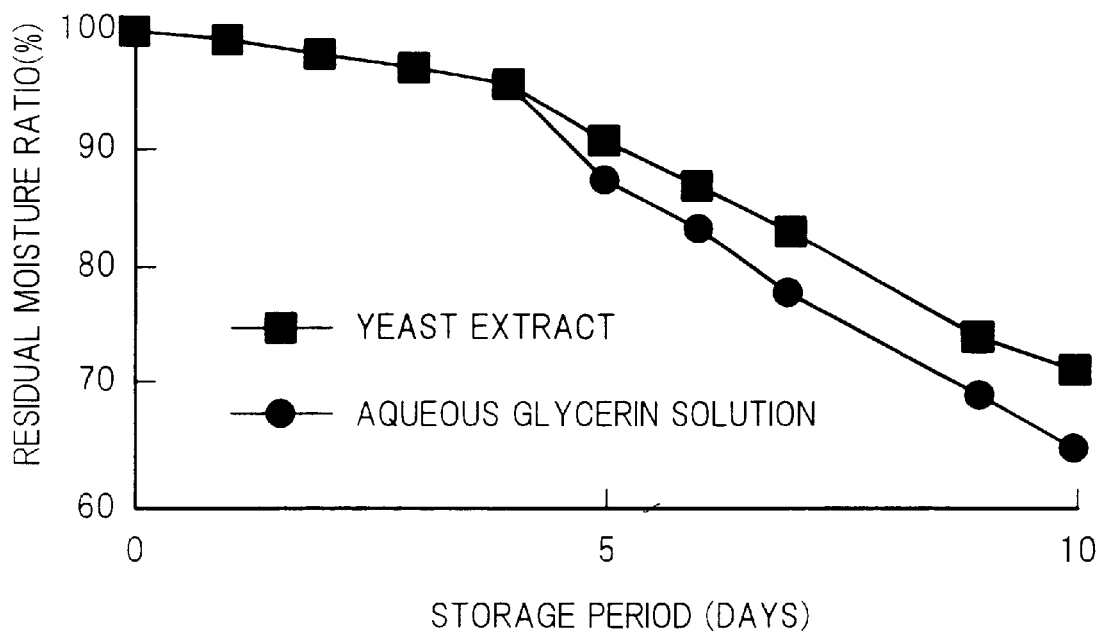
FIG. 1 depicts the residual moisture ratio at the moisture evaporation test of the yeast extract in Example 6.

Any yeast extract solution recovered by any conventional method may be used as a raw material according to the method of the present invention. More specifically, those yeast extract solutions produced by any method including autolysis methods, enzymatic decomposition methods by using enzymes such as proteinase, glucanase and nuclease, and chemical treatments including acid or alkali decomposition may satisfactorily be used as the raw materials in accordance with the present invention.

Any yeast may be used for producing the extract solution, with no specific limitation; any yeast for general use in producing yeast extract, for example, brewery yeast, baker's yeast, and Torula yeast, may be used satisfactorily.

Furthermore, not only yeast freshly cultured for producing a yeast extract but also yeast after the brewing of beer and Japanese sake may also be used. Because the yeast after the use for beer brewing contains bitterness and astringent taste derived from hop, the yeast is preferably treated with processes such as rinsing process in water and other treatments for removing the bitterness, for subsequent use in producing a yeast extract. Not only fresh yeast but also dry yeast produced by drum drying or spray drying may also be used as a raw material.

The inventive method using the yeast extract solution is described in detail.

The heating process is for coloring the yeast extract solution, wherein the yeast extract solution is generally treated at a high temperature for a short period of time. More specifically, the yeast extract solution is subjected to heating treatment at 60 to 150° C., preferably 100 to 150° C. for 20 seconds to 30 minutes, preferably one to 10 minutes. Thus, colored substances are thereby produced by aminocarbonyl reaction etc., and the yeast extract solution can be sterilized.

After the heating process, the colored yeast extract solution may then be subjected to a process of removing solids produced at the heating process, prior to the adsorption process of putting the colored yeast extract solution in contact to an ion exchange resin to remove the colored substances in the yeast extract solution. In other words, the solids produced during the above reaction are mainly insoluble proteins and the like, and they can be removed by procedures for putting the solids and high molecular substances remaining in the extract solution in contact to an organic solvent miscible with water, such as alcohols, like ethanol, methanol etc. or acetone, to precipitate the solids and high molecular substances. Besides, the solids can be removed by ultrafiltration or membrane treatments with loose reverse osmotic membrane and the like. Such preliminary process when employed can prevent troubles such as clogging at the contact process thereof with an ion exchange resin for use at the next process, and owing to the process, additionally, use may conveniently be made of an ion exchange resin with an ion exchange capacity not so high and therefore with no potency to adsorb amino acid and the like, which are essentially present in yeast extract.

Similar advantages may be expected, if a concentration process of the yeast extract solution and a solid-liquid separation process are arranged prior to the heating process, to preliminarily remove coloring substances, low-solubilizable substances and impurities from the raw material yeast extract solution.

The adsorption process for putting the colored yeast extract solution in contact to an ion exchange resin to remove the colored substances in-the yeast extract solution is a process for putting the yeast extract solution in contact to a resin with an ion exchange group, to adsorb the colored substances present (or remaining when the preliminary removal process is carried out) in the yeast extract solution on the resin to thereby remove the colored substances.

As the ion exchange resin to be used at the process, those never adsorbing amino acids as the useful component in the yeast extract should be selected, and furthermore, a hydrophobic carrier is more preferably used so as to deodorize the yeast extract solution and remove the bitterness therefrom. For use, additionally, the ion exchange resin is preferably mounted on a supporter, and as the supporter, preferably, use is made of those capable of removing unique odorous components present in the yeast extract solution, such as synthetic resins with hydrophobic groups and active charcoal.

As the conditions for treating the yeast extract solution with such ion exchange resin, preference is given to conditions for putting the yeast extract solution in contact to the resin as long as possible. So as to recover a yeast extract within a permissible range as nearly colorless, the flow rate is preferably 2.0 or less on a spatial linear velocity (SV) basis, while the flow volume is preferably 10-fold or less the volume of the resin.

The yeast extract with the decrease in color and odor, thus recovered, can be prepared into products, as it is or after it is concentrated to an appropriate concentration. So as to prevent contamination with infectious microbe during storage, furthermore, an appropriate preservative is possibly added to such extract, depending on the objective.

By drying the yeast extract by spray drying or freeze-drying, furthermore, the storability thereof can be enhanced. When the resulting yeast extract is exposed to a high temperature at the concentration process or drying process, however, the yeast extract might potentially be colored again. Therefore, the temperature conditions therefor should be selected appropriately.

Compared with an untreated yeast extract, the yeast extract thus recovered by the present invention is apparently colorless or colored slightly pale yellow with almost no odor, at a solid content of 10%, although the amino acids therein are hardly lost. As has been described above, no color or odor is observed in the resulting yeast extract, and when the yeast extract is used as a seasoning, therefore, the extract is readily mixed with other materials for use as a Japanese-style seasoning. It has been very difficult to use conventional yeast extract for such Japanese-style seasoning, because of the color and odor of conventional yeast extract. Additionally, the resulting yeast extract can be added as a cosmetic material to cream, emulsion and the like, and additionally to white or transparent liquids such as skin lotion. Besides, the yeast extract can be utilized in healthy drinks, healthy food material and bathing agent.

As has been described above, the yeast extract produced in accordance with the present invention is applicable to new uses other than the uses of conventional yeast extract, so it is expected that the applicable range of yeast extract itself may be enlarged.

Then, the present invention will now be described in examples, but the present invention is not limited to these examples.

EXAMPLE 1

(1) Heating process

Beer yeast after the use for beer brewing was centrifuged (at 3,000 rpm for 10 minutes) to remove the beer fraction, and then, water was added to the resulting yeast to a final yeast concentration of 40%, which was used as a raw material.

150 L of the raw material were subjected to autolysis at 55° C. for 48 hours and subsequent centrifugation (at 3,000 rpm for 10 minutes) to remove the solids therein, to recover a liquid fraction of 95 L. Continuously, the resulting liquid fraction was concentrated to 20 L with a use of rotary evaporator, which was then subjected to a heating process at 120° C. for 30 seconds.

(2) Filtration process

The colored yeast extract solution recovered in above (1) was preliminarily passed through a sieve of 100 mesh to remove large solids therein, followed by removal of the high molecular substances in the yeast extract solution by using a loose reverse osmotic membrane at a sodium chloride blocking ratio of 10% while water was added to the yeast extract solution, to recover a dark brown yeast extract at a solid content of 10% at a yield of 50 L.

(3) Adsorption process

5 L of the yeast extract solution recovered in above (2) were subjected to an adsorption process comprising passing the extract solution through a column packed with an ion exchange resin on a support active charcoal and eluting the yeast extract within 2 hours. At the operation, the spatial linear velocity was set to 1.0; the resin volume was set to 2.5 L and the flow ratio was set to 2.0. Furthermore, by passing water at the same flow rate for one hour, a slightly pale yellow yeast extract (at a solid content of 7%) with no odor was recovered at a yield of 7.5 L.

Prior to and after the adsorption process, the yeast extract was examined in terms of liquid volume, solid content, chromaticity, total amino acid and odor. Herein, the color is represented as the absorbance at 420 nm, while the content of total amino acids is represented in % in the anhydrous yeast extract. The results are shown in Table 1. The content of sugars in the yeast extract was 0.0% after the adsorption process.

TABLE 1

|  | Prior to adsorption process | After adsorption process |
| --- | --- | --- |
| Liquid volume | 10 L | 7.5 L |
| Solid content | 10.0% | 8.5% |
| Degree of color[1] | 0.23 | 0.01 |
| Total amino acids[2] | 53% | 57% |
| Odor | yeast odor | almost odorless |

[1]Absorbance at 420 nm
[2]Total amino acids in % in the anhydrous yeast extract As a result, no difference in solid content and total amino acids was observed between prior to and after the adsorption process. However, apparent difference in color and odor was observed between prior to and after the adsorption process, which indicates that the yeast extract of the present invention is better.

EXAMPLE 2

Except that the spatial linear velocity was set at 2.0 and the flow ratio was set at 4.0 at the adsorption process in Example 1(3), all the procedures were carried out in the same manner as in Example 1, whereby about 25 L of yeast extract (at a solid content of 7.1%), pale yellow and slightly odorous, was recovered. The color and the contents of sugars and total amino acids of the resulting yeast extract were determined, and the results are shown in Table 2.

EXAMPLE 3

In the same manner as in Example 1, beer yeast after beer brewing was centrifuged (at 3,000 rpm for 10 minutes) to remove the beer fraction, and water was added to the resulting yeast to a final yeast concentration of 40%, which was then used as a raw material.

100 L of the raw material were subjected to autolysis at 55° C. for 48 hours, followed by centrifugation (at 3,000 rpm for 10 minutes) to remove solids therefrom, to recover a liquid fraction of 95 L. Then, the liquid fraction was concentrated to 20 L, by using a rotary evaporator. To the concentrated solution was gradually added an equal volume of ethanol, and the resulting mixture was left to stand, to remove precipitates to recover the supernatant. From the supernatant ethanol was removed by using a rotary evaporator, and water was added to the resulting matter to a final solid content of 10%.

5 L of the resulting yeast extract solution were subjected to an adsorption process under the same conditions as in Example 1(3). Consequently, pale yellow and odorless yeast extract (at a solid content of 6.9%) was recovered at a yield of 7.5 L. Conditions other than those described above were the same as in Example 1. Table 2 shows the degree of color and the contents of sugars and total amino acids of the obtained yeast extract.

EXAMPLE 4

By using a plain ultrafiltration membrane of a cross-flow type of a molecular fractionation of 10,000 instead of the loose reverse osmotic membrane in Example 1, filtration was carried out while water was added, to recover a dark brown yeast extract solution at a solid content of 10% at a yield of 45 L.

5 L of the yeast extract solution were subjected to an adsorption process under the same conditions as in Example 1(3). Consequently, a pale yellow and odorless yeast extract (at a solid content of 7%) was recovered at a yield of 7.5 L. All the conditions other than those described above were the same as in Example 1. The degree of color and the contents of sugars and total amino acids of the resulting yeast extract were determined, and the results are shown in Table 2.

EXAMPLE 5

1 kg of dry yeast was suspended in 10 L of water, and by using hydrochloric acid, the resulting suspension was adjusted to pH 5. Then, proteinase and nuclease were added to the resulting suspension, which was then retained at 52° C. for 16 hours, to extract the contents. Subsequently, the contents were centrifuged (at 3,000 rpm for 10 minutes) to remove solids, to yield an extract solution at 6 L. From the extract solution were removed high molecular substances by using a loose reverse osmotic membrane, and the obtained solution was rinsed in water, to recover a dark brown yeast extract solution at a solid content of 10% at a yield of 9 L.

5 L of the resulting yeast extract solution were subjected to an adsorption process in the same manner as in Example 1(3), to recover a pale yellow and odorless yeast extract (at a solid content of 7.5%) at a yield of 7.5 L. The degree of color and the contents of sugars and total amino acids of the resulting yeast extract were determined, and the results are shown in Table 2.

TABLE 2

|  | Example 2 | Example 3 | Example 4 | Example 5 |
| --- | --- | --- | --- | --- |
| Solid content (%) | 7.1 | 6.9 | 5.6 | 7.5 |
| Degree of color[1] | 0.08 | 0.01 | 0.02 | 0.02 |
| Content of sugars (%) | 1 | 0 | 0 | 0.3 |
| Content of total amino acids[2] | 55 | 42 | 39 | 43 |
| Color of yeast extract | yellow | pale yellow | pale yellow | pale yellow |
| Odor of yeast extract | slight yeast odor | odorless | odorless | odorless |

[1]Absorbance at 420 nm
[2]Content of total amino acids in % in the anhydrous yeast extract

EXAMPLE 6

The moisture retaining ability of the yeast extract prepared in Example 1 was examined (the moisture evaporation was determined and a water loading test on the skin layer was conducted).

(1) Determination of moisture evaporation 5 ml of the yeast extract prepared in Example 1 was placed in a beaker, which was then stored under the condition of 80% relative humidity at 25° C. for 4 days. Subsequently, the yeast extract was transferred into a silica gel desiccator (at 25° C.), for periodic determination of the residual moisture to calculate moisture evaporation. As a control, furthermore, 5% glycerin solution as a moisturizing agent was subjected to the same test. The results are shown in FIG. 1. In the figure, -■- expresses the case of the yeast extract and -●- expresses the case of the aqueous glycerin solution.

As apparently shown in FIG. 1, on day 5 after the extract was transferred to dry condition and thereafter, the residual moisture ratio in the yeast extract produced in accordance with the present invention was higher than that of control, which indicates that the yeast extract had a moisture retaining effect at same level as or at higher level than the level of glycerin solution.

(2) Water loading test over the horny layer

Figure 2:
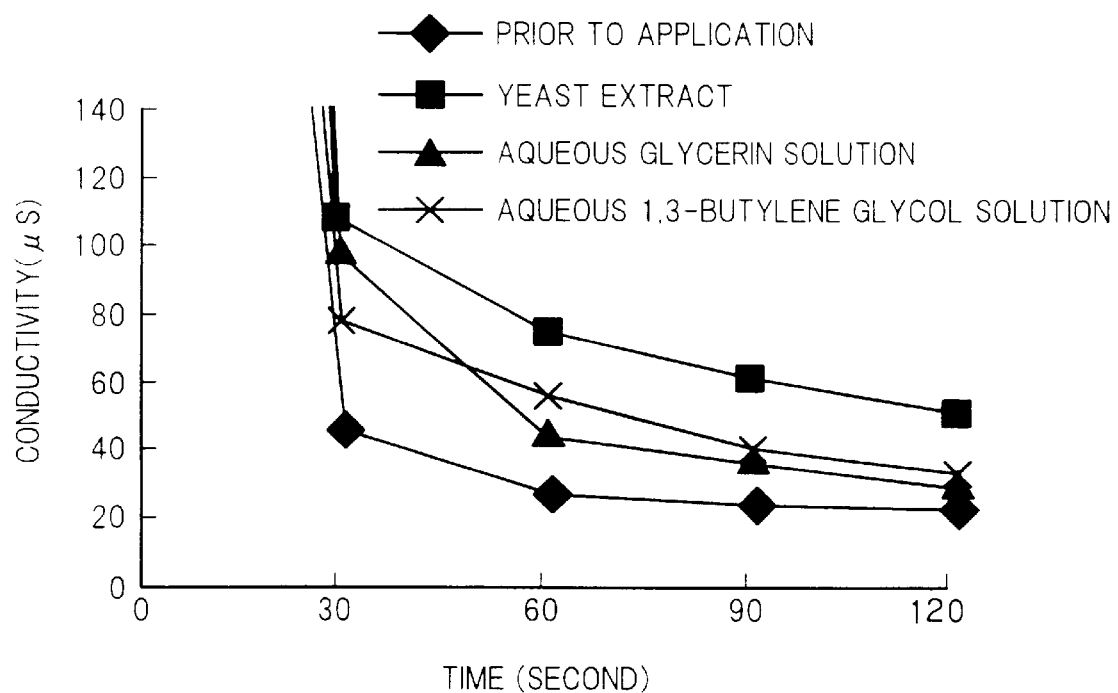
FIG. 2 depicts the conductivity change with a lapse of time at the water loading test on the skin in Example 6.

The yeast extract recovered by the inventive method was prepared into a 5% solution, which was then applied in 3 ml portions to coat on the forearm bending side of 5 test subjects. After the testing site was dried, one drop of distilled water was dropped on the site and surplus water was then removed 10 seconds later. Immediately thereafter, the conductivity level (moisture content) was measured by using a high-frequency conductometry analyzer manufactured by Shimadzu) every 30 seconds over 2 minutes. As controls, an aqueous 5% glycerin solution and an aqueous 5% 1,3-butylene glycol solution were also subjected to the same test. FIG. 2 shows the change of conductivity with a lapse of time. In the figure, -♦- expresses the conductivity prior to application; -■- expresses the conductivity when the yeast extract was applied; -▲- expresses the conductivity when the aqueous glycerin solution was applied; and -×- expresses the conductivity when the aqueous 1,3-butylene glycol solution was applied.

As apparently shown in FIG. 2, a higher water retaining potency was confirmed when the inventive yeast extract was applied, compared to the case prior to application and the control case. Those described above indicate that the inventive yeast extract has a moisture retaining ability at same level as or at higher level than the level of polyhydric alcohol when blended in a cosmetic product.

EXAMPLE 7

By assaying the inhibitory activity of the yeast extract of Example 1 to tyrosinase, the potency to inhibit pigment deposition was examined. First, reaction systems 1 to 3 containing L-tyrosine as a substrate as shown in Table 3 were prepared.

Continuously, the reaction mixture was kept at 25° C. for 10 minutes, to measure the absorbance at a wave length of 475 nm to calculate the enzyme inhibition ratio.

Figure 3:
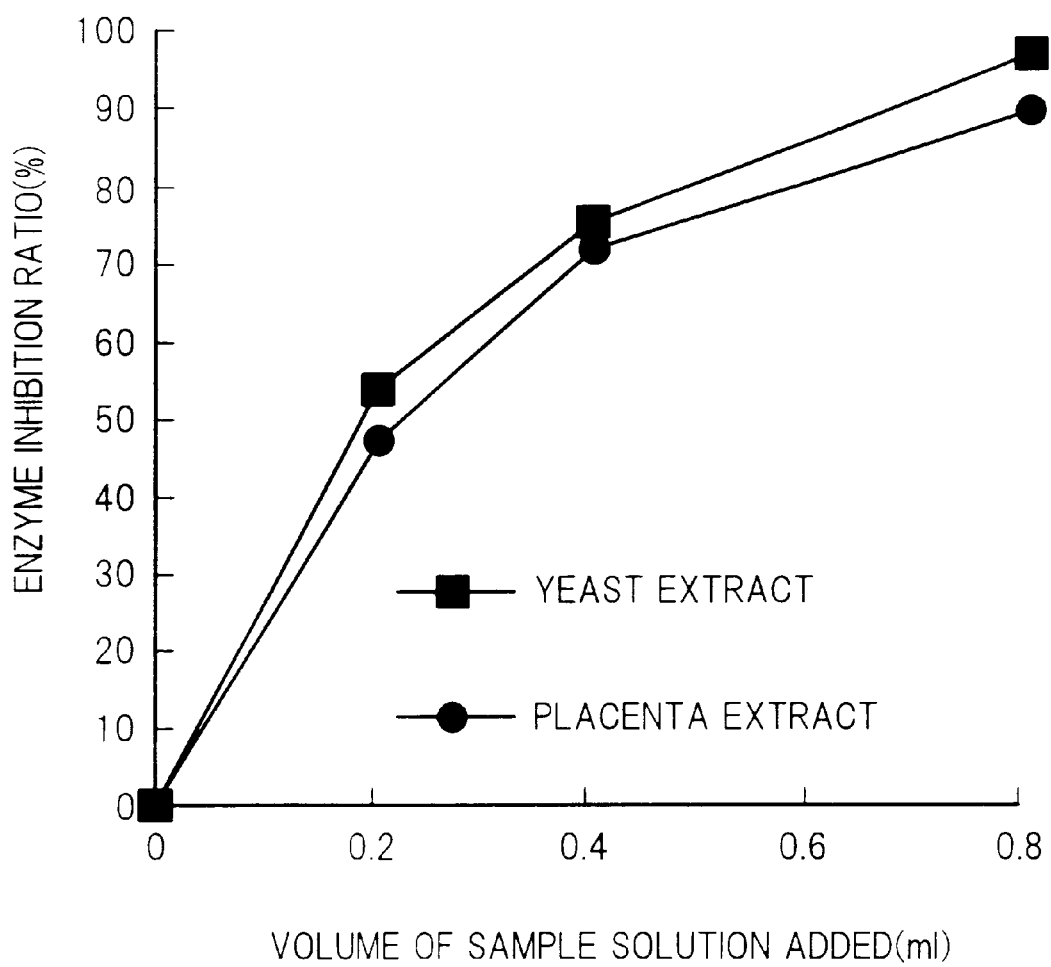
FIG. 3 depicts the inhibitory activity of the yeast extract to tyrosinase in Example 7.

The relation between the enzyme inhibition ratio and the amount of the yeast extract added is shown in FIG. 3. Furthermore, a commercially available placenta extract instead of the yeast extract was used as a control and was then subjected to the same test. In the figure, -■- expresses the case of the yeast extract and -●- expresses the case of placenta extract.

As apparently shown in FIG. 3, the yeast extract exerted the tyrosinase inhibitory activity at almost the same level as the level exerted by the placenta extract.

TABLE 3

|  | 1 | 2 | 3 |
|---|---|---|---|
| 1.5 mM L-Tyrosine (ml) | 0.4 | 0.4 | 0.4 |
| 0.07 M Phosphate buffer (pH 6.8) (ml) | 2.3 | 2.1 | 1.7 |
| Tyrosinase (2,000 U/ml)*) (ml) | 0.1 | 0.1 | 0.1 |
| Yeast extract of Example 1 | 0.2 | 0.4 | 0.8 |

*)derived from mushroom

EXAMPLE 8

20 ml of the yeast extract prepared in Example 1 was placed in a closely sealed container and was then stored at 50° C. for 3 months (in darkness). The change of the color of the yeast extract after storage was evaluated by measuring the absorbance at a wave length of 420 nm whereby the stability was assessed. The change of the absorbance during the storage period is shown in FIG. 4.

Figure 4:
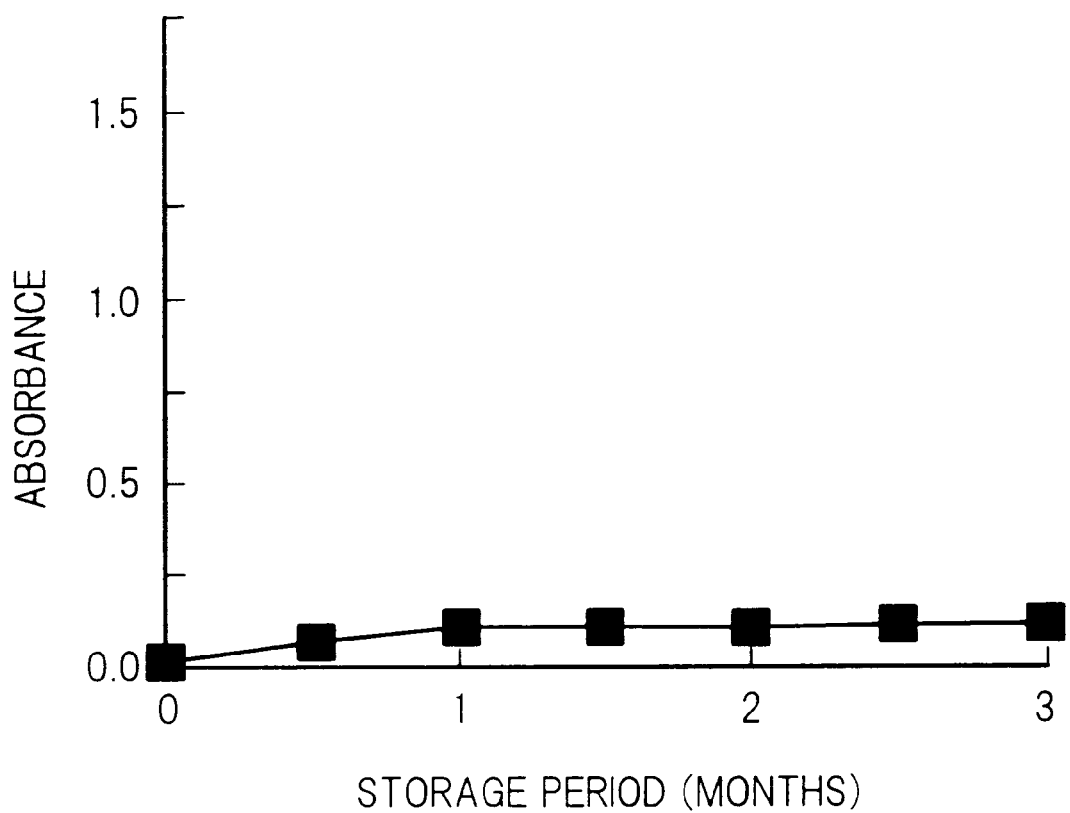
FIG. 4 depicts the stability of the yeast extract in Example 8.

As apparently shown in FIG. 4, almost no change was observed in absorbance even after three months, and the inventive yeast extract retained its stable quality during the long-term storage.

PRODUCTION EXAMPLE 1

By using the yeast extract produced in Example 1, a skin lotion of the formulation shown in Table 4 was prepared in a conventional manner.

TABLE 4

| Components | Amount to be blended (%) |
|---|---|
| Yeast extract | 5.0 |
| Preservative | 0.15 |
| Alcohols | 5.0 |
| Perfume | 0.02 |
| Other additives | 4.83 |
| Distilled water | 85.0 |
| Total | 100.0 |

EXAMPLE 9

Sixteen female panelists (age 20 to 39) used the skin lotion prepared in the Production Example 1, to answer the questionnaires about their impressions over the use thereof. As a control, furthermore, a skin lotion without yeast extract was produced in the same manner as in the Production Example 1 (the amount of distilled water in Table 4:90.0%), which was then used.

The questionnaires were about 4 items, namely odor, wet touch, no sticky feeling, and general assessment, so that the panelists picked up any one of the following replies; the skin lotion of the Production Example 1 is better; the control skin lotion is better; and no difference. The number of panelists for each reply was counted, to make the assessment. The results are shown in Table 5.

TABLE 5

|  | Skin lotion of Production Example 1 | Control skin lotion | No difference |
|---|---|---|---|
| Odor | 8 persons | 7 persons | 1 person |
| Wet touch | 5 persons | 7 persons | 4 persons |
| No sticky feeling | 9 persons | 4 persons | 3 persons |
| General assessment | 11 persons | 4 person | 1 person |

Comparing the cosmetic product of the Production Example 1, namely the cosmetic product using the inventive yeast extract, with the control, consequently, the product and the control were ranked at almost the same level in terms of odor and wet touch, but in terms of less sticky feeling after use, the skin lotion with the inventive yeast extract added thereto got higher assessment, and in terms of general assessment, furthermore, the skin lotion with the inventive yeast extract added thereto got far higher assessment.

An organoleptic test was conducted over the change of the effect of the inventive yeast extract, depending on the amount of the yeast extract blended into the skin lotion. As a result, 3 of the 16 panelists remarked the difference in wet touch between the skin lotion with the yeast extract blended therein at 0.5% (at the amount of distilled water blended therein being 89.5% and the skin lotion with the yeast extract blended therein at less than 0.5%, while 10 of the panelists remarked the presence of wet touch and the absence of sticky feeling when the amount of the yeast extract blended therein was set at 1.0%.

10 of the panelists remarked the presence of sticky feeling about the skin lotion at the amount of the yeast extract blended therein above 10%.

Industrial Applicability

In accordance with the present invention, color and characteristic odor can be removed in a simple fashion from the yeast extract solution recovered in a conventional manner, with no loss of the contents of useful substances such as amino acid, etc. Because the resulting yeast extract can be mixed with other materials for use, the yeast extract is applicable to various fields, for example for cosmetic products and healthy foods, other than seasonings, and accordingly, the applicable range of the yeast extract is expectantly enlarged.

We claim:

1. A method of preparing a cosmetic composition, comprising:

heating a yeast extract solution at a temperature of 100° C. to 150° C. for 20 seconds to 30 minutes, wherein colored substances are produced in the yeast extract solution;

contacting the heated yeast extract solution with an ion exchange resin to remove colored substances from the yeast extract solution; followed by recovering the yeast extract solution and incorporating the recovered yeast extract into a cosmetic composition.

2. The method of claim 1, wherein the yeast extract solution is heated at a temperature of 100° C. to 150° C. for one to 10 minutes.

3. The method for of claim 1, wherein the ion exchange resin comprises a supporter made from a material having an odor absorbing function, into which an ion exchange group is introduced.

4. The method of claim 1, wherein the solids concentration of the yeast extract solution is adjusted to 40% or higher prior to said heating.

5. The method of claim 4, wherein solids concentration of the yeast extract solution is adjusted by concentrating the yeast extract solution and solid-liquid separating the concentrated yeast extract solution.

6. A method of preparing a cosmetic composition, comprising:

heating a yeast extract solution at a temperature of 100° C. to 150° C. for 20 seconds to 30 minutes, wherein colored substances and solids are produced in the yeast extract solution;

filtering the heated yeast extract solution to remove solids and high molecular weight substances from the solution;

contacting the filtered yeast extract solution with an ion exchange resin to remove colored substances from the yeast extract solution; followed by recovering the yeast extract solution and incorporating the recovered yeast extract into a cosmetic composition.

7. The method of claim 6, wherein the yeast extract solution is heated at a temperature of 100° C. to 150° C. for one to 30 minutes.

8. The method of claim 6, wherein said filtering comprises an ultrafiltration.

9. The method of claim 6, wherein said filtering comprises contacting the heated yeast extract solution with a loose reverse osmotic membrane.

10. The method for of claim 6, wherein the ion exchange resin comprises a supporter made from a material having an odor absorbing function, into which an ion exchange group is introduced.

11. The method of claim 6, wherein the solids concentration of the yeast extract solution is adjusted to 40% or higher prior to said heating.

12. The method of claim 11, wherein solids concentration of the yeast extract solution is adjusted by concentrating the yeast extract solution and solid-liquid separating the concentrated yeast extract solution.

13. A method of preparing a cosmetic composition, comprising:

heating a yeast extract solution at a temperature of 100° C. to 150° C. for 20 seconds to 30 minutes, wherein colored substances and solids are produced in the yeast extract solution;

contacting the heated yeast extract solution with an organic solvent miscible with water to precipitate solids and high molecular weight substances in the yeast extract solution;

contacting the yeast extract solution with an ion exchange resin to remove colored substances from the yeast extract solution; followed by recovering the yeast extract solution and incorporating the recovered yeast extract into a cosmetic composition.

14. The method of claim 13, wherein the yeast extract solution is heated at a temperature of 100° C. to 150° C. for one to 30 minutes.

15. The method for of claim 13, wherein the ion exchange resin comprises a supporter made from a material having an odor absorbing function, into which an ion exchange group is introduced.

16. The method of claim 13, wherein the solids concentration of the yeast extract solution is adjusted to 40% or higher prior to said heating.

17. The method of claim 16, wherein solids concentration of the yeast extract solution is adjusted by concentrating te yeast extract solution and solid-liquid separating the concentrated yeast extract solution.

18. A cosmetic product obtained by the method of claim 11.

19. A cosmetic product obtained by the method of claim 16.

20. A cosmetic product obtained by the method of claim 13.

* * * * *